(12) United States Patent
Randall

(10) Patent No.: US 7,799,024 B2
(45) Date of Patent: Sep. 21, 2010

(54) TISSUE ABLATION PROBES AND METHODS FOR TREATING OSTEOID OSTEOMAS

(75) Inventor: Kerryn Randall, Broomfield, CO (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 832 days.

(21) Appl. No.: 11/617,570

(22) Filed: Dec. 28, 2006

(65) Prior Publication Data

US 2007/0185484 A1 Aug. 9, 2007

Related U.S. Application Data

(60) Provisional application No. 60/755,663, filed on Dec. 29, 2005.

(51) Int. Cl.
*A61B 18/12* (2006.01)
(52) U.S. Cl. .............. 606/41; 606/45; 606/46; 606/48
(58) Field of Classification Search .......... 606/45, 606/48, 51–52
See application file for complete search history.

(56) References Cited

U.S. PATENT DOCUMENTS

2004/0059328 A1* 3/2004 Daniel et al. .............. 606/41

OTHER PUBLICATIONS

Office Action dated Jul. 1, 2009 in European Patent Application No. 06 850 371.3-2305, Applicant: Boston Scientific Limited, (3 pages).

PCT International Search Report dated Dec. 20, 2007 for related International Application Serial No. PCT/US2006/062681 filed Dec. 28, 2006, Inventor Kerryn Randall (3 pages).
PCT Written Opinion dated Dec. 20, 2007 for related International Application Serial No. PCT/US2006/062681 filed Dec. 28, 2006, Inventor Kerryn Randall (6 pages).
International Preliminary Report on Patentability (Chapter I of the Patent Cooperation Treaty) issued by The International Bureau for related International Appln. No. PCT/US2006/062681, Applicant: Boston Scientific Limited, dated Jul. 10, 2008 (7pages).

* cited by examiner

*Primary Examiner*—Linda C Dvorak
*Assistant Examiner*—Jaymi Della
(74) *Attorney, Agent, or Firm*—Vista IP Law Group LLP

(57) ABSTRACT

A method of treating bone tissue (e.g., a tumor, such as an osteoid osteoma) is provided. The method comprises introducing an ablation probe into bone tissue, deploying at least one ablative element transversely from the probe into the bone tissue, and conveying ablation energy from the ablative element(s) to ablate the bone tissue. In one method, the ablative element(s) comprises a pair of ablative elements, in which case, the ablative elements are transversely deployed from the ablation probe in opposite directions. In another method, the ablative element(s) comprises a plurality of ablative elements, in which case, the ablative elements are transversely deployed outward from the ablation probe in a plane. The ablation energy conveyed from the ablative element(s) may have a non-spherical profile, e.g., an elongated profile, to match a non-spherical profile of the bone tissue to be treated.

17 Claims, 6 Drawing Sheets

TISSUE ABLATION PROBES AND METHODS FOR TREATING OSTEOID OSTEOMAS

CROSS-REFERENCE TO RELATED APPLICATIONS

This application claims the benefit under 35 U.S.C. §119 to U.S. Provisional Application Ser. No. 60/755,663, filed on Dec. 29, 2005 which is incorporated herein by reference.

FIELD OF INVENTION

The present invention relates generally to tissue ablation devices and, more specifically, to tissue ablation probes for ablating tissue, such as cancerous bone tissue.

BACKGROUND

Osteoid osteomas are benign, but painful, tumors that mainly occur in children and young adolescents, accounting for 10-12 percent of benign bone tumors with 80 percent of patients being between 5-24 years of age. Most osteoid osteomas are elongated in shape, have little or no growth potential, and rarely exceed 1.5 centimeters in diameter. There are typically three approaches to treatment: (1) medical treatment, which includes the administration of aspirin or other nonsteroidal anti-inflammatory agents that can be used in the long term; (2) surgical treatment, which involves resecting the tumor from the bone; and (3) radio frequency (RF) treatment, which involves percutaneously inserting an ablation needle within the bone and ablating the tumor with RF energy.

With regard to medical treatment, the pain is often intolerable and long-term use of nonsteroidal anti-inflammatory agents can result in gastrointestinal side effects. Surgery can be challenging due to difficulties in identification, incomplete removal of the tumor, and the adverse effect of the resection on a weight-bearing bone. RF ablation has become the method preferred by most doctors, because of its percutaneous, less invasive advantages. This technology allows the tumor to be ablated (burnt) by an electrode that is placed in the center of the nidus of the tumor.

Currently, percutaneous RF ablation can be accomplished using a multiple needle electrode probe or a single needle electrode probe. Multiple needle electrode probes are intended for soft tissue tumors and are somewhat limited in bone tumor applications, mainly due to the relatively small size of osteoid osteomas and the difficulty of penetrating the hard bone tissue with the relatively flexible electrodes. Although the size and hard tissue penetration considerations of single needle electrode probes are more ideal, the greatest challenge when using single-needle probes is to create the largest ablation area to coincide with the elongated geometry of the tumor. However, because single needle electrodes tend to favor a spherical ablation, the elongated osteoid osteomas must be treated with multiple ablations, requiring the electrode to be repositioned for subsequent ablations in order to prevent or minimize the destruction of healthy tissue.

There, thus, remain a need to provide tissue ablation probes and tissue ablation methods for treating tumors within bone tissue, such as osteoid osteomas.

SUMMARY OF INVENTION

In accordance with one aspect of the present inventions, a method of treating bone tissue (e.g., a tumor, such as an osteoid osteoma) is provided. The method comprises introducing an ablation probe into bone tissue (e.g., percutaneously), deploying at least one ablative element transversely from the probe into the bone tissue, and conveying ablation energy from the ablative element(s) to ablate the bone tissue. In one method, the ablative element(s) comprises a pair of ablative elements, in which case, the ablative elements are transversely deployed from the ablation probe in opposite directions. In another method, the ablative element(s) comprises a plurality of ablative elements, in which case, the ablative elements are transversely deployed outward from the ablation probe in a plane. The ablation energy conveyed from the ablative element(s) may have a non-spherical profile, e.g., an elongated profile, to match a non-spherical profile of the bone tissue to be treated.

The ablative element(s) may have any configuration that allows them to be transversely deployed from the ablation probe. For example, each ablative element may comprise a distal tip that can be deployed into the bone tissue by advancing the distal tip through the bone tissue. Or, each ablative element may be deployed into the bone tissue by bowing the ablative element transversely outward from the ablation probe. In the latter case, each ablative element may comprise a tissue cutting edge that cuts through the bone tissue as the ablative element is radially bowed outward from the ablation probe. In an optional method, the ablative element(s) are deployed incrementally, and ablation energy is conveyed from the ablative element(s) between incremental deployments of the ablative element(s).

In accordance with another aspect of the present inventions, another method of treating bone tissue (e.g., a tumor, such as an osteoid osteoma) is provided. The method comprises introducing a probe into bone tissue, e.g., percutaneously, deploying at least one electrode transversely from the probe into the bone tissue, and conveying radio frequency (RF) energy from the electrode element(s) into the bone tissue. The electrode element(s) may be arranged in the same manner as the ablative element(s) discussed above. The RF energy conveyed from the electrode element(s) has a therapeutic effect, e.g., by ablating the bone tissue.

Other and further embodiments and aspects of the invention will become apparent when reviewing the following detailed description.

BRIEF DESCRIPTION OF THE DRAWINGS

Various embodiments of the invention are disclosed in the following detailed description and in the accompanying drawings, which may not be drawn to scale, and in which.

DETAILED DESCRIPTION OF THE ILLUSTRATED EMBODIMENTS

Figure 1:
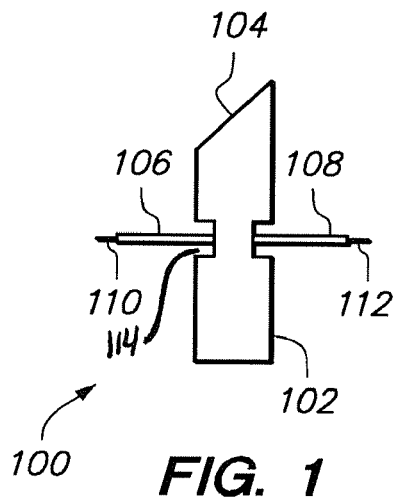
FIG. 1 is a plan view of an ablation probe constructed in accordance with one embodiment of the present inventions.

FIG. 1 illustrates a tissue ablation probe 100 constructed in accordance with one embodiment of the present inventions. The tissue ablation probe 100 comprises a delivery cannula 102 having a distal portion 104, and electrodes 106 and 108 transversely deployable from a plurality of openings 114 in the side of the cannula 102. Optional coverings (not shown) may be provided over the openings 114. In one embodiment, the electrodes 106 and 108 are mounted to an inner probe shaft (not shown) reciprocatably disposed within the cannula 102. Thus, distal movement of the inner probe shaft relative to the cannula 102 deploys the electrodes 106 and 108 transversely outward from the cannula 102 collinearly in opposite directions, and proximal movement of the inner probe shaft relative to the cannula 102 retracts the electrodes 106 and 108 within the cannula 102.

Deployment may be adjusted for various burn widths, depending upon the size and dimensions of a target body. For example, if the osteoid osteoma to be treated is approximately 1 cm in width and 1 cm in length, the electrodes 106 and 108 may be deployed from the cannula 102 a minimal distance to create a matching circular ablation. If the osteoid osteoma to be treated is approximately 1 cm in width and 1.5 cm in length, the electrodes 106 and 108 may be deployed from the cannula 102 further to create a matching elliptical ablation. If the osteoid osteoma to be treated is approximately 1 cm in width and 2.0 cm in length, the electrodes 106 and 108 may be deployed from the cannula 102 even further to create a more elongated matching elliptical ablation.

In an optional embodiment, additional electrodes may be provided, such that the electrodes can extend transversely outward from the cannula 102 in a plane. For example, a total of four electrodes may be provided, such that a 90 degree angle is formed between each adjacent pair of electrodes.

In the illustrated embodiment, the electrodes 106 and 108 are insulated and have exposed electrode tips 110 and 112 to focus RF energy at the tips of the electrodes 106 and 108. Insulation may also ensure that short circuits do not occur when electrodes are fully retracted within cannula 102. When inserting the ablation probe 100 into the patient's body, the distal portion 104 of the cannula 102 may have a tip or other penetrating surface that aids insertion or placement into a tissue body or region (e.g., malignant or benign cancerous tissue such as an osteoid osteoma).

Once inserted (e.g., into the nidus of a tumor), the ablation probe 100 may be coupled to a power source and RF energy may be supplied along wires or filaments of electrodes 106 and 108. Once deployed, RF energy may be transmitted along electrodes 106 and/or 108 into target tissue. In some embodiments, a bipolar electrode configuration may be implemented with ablation probe 100, with one of tips 110 or 112 acting as a supply (e.g., positive lead) and the other tip acting as a return. In other embodiments, a monopolar electrode configuration may be implemented. In a monopolar configuration, tips 110 and 112 are positive leads (i.e., "live") and current flows from tips 110 and 112 to a grounding pad placed on the patient's body. By adjusting the deployed length of electrodes 106 and 108 into a target region, an adjustable ablation burn pattern may be achieved to treat irregularly-shaped tumors, tissues, bones, and tissue bodies.

Thus, it can be appreciated that because the electrodes 106 and 108 transversely extend outward from the cannula 102 in opposite directions, RF energy delivered to or between the electrodes 106 and 108 has an elongated profile. In the case where more electrodes are provided, some of the electrodes can be shorter than others to maintain the elongated profile of RF energy. For example, if four electrodes are utilized, one opposing pair of the electrodes can be longer than the remaining opposing pair of electrodes.

Figure 2:
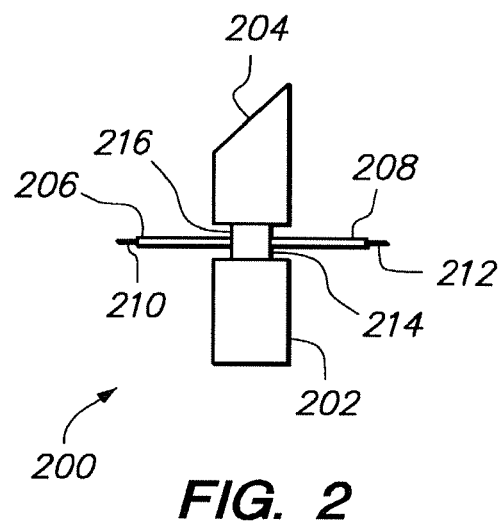
FIG. 2 is a plan view of an ablation probe constructed in accordance with another embodiment of the present inventions.

FIG. 2 illustrates a tissue ablation probe 200 constructed in accordance with another embodiment of the present inventions. The ablation probe 200 includes an outer cannula having proximal portion 202 and distal portion 204. The ablation probe 200 also includes electrodes 206 and 208 with respective electrode tips 210 and 212, and an inner cannula 214. Here, the inner cannula 214 may be configured to separate, slide, or move proximal portion 202 and distal portion 204 away from each other to provide an opening 216 out which the electrodes 206 and 208 may be deployed.

When proximal portion 202 and distal portion 204 are moved together, the opening 216 closes. For example, electrodes 206 and 208 may retract into inner cannula 214 and then proximal portion 202 and distal portion 204 are moved together, closing the opening 216 and forming a seal between proximal portion 202 and distal portion 204. In some embodiments, a seal may also include a gasket for creating a non-tight, air-tight, water-tight, or other type of seal between proximal portion 202 and distal portion 204 when fully retracted. In other embodiments, when the opening 216 between proximal portion 202 and distal portion 204 is closed, ablation probe 200 may be inserted or retracted into tissue within a target region. Like the ablation probe 100, the ablation probe 200 may have a monopolar or bipolar electrode configuration, and may have more than two electrodes.

Figure 3:
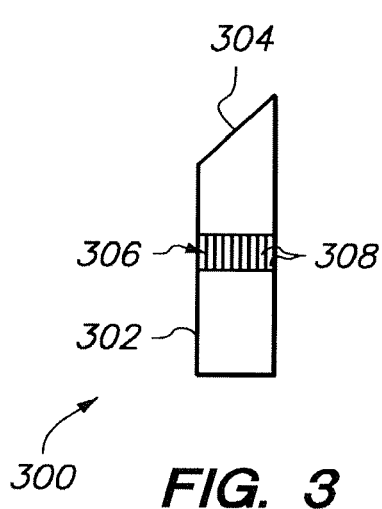
FIG. 3 is a plan view of an ablation probe constructed in accordance with still another embodiment of the present inventions, wherein ablative elements are particularly shown in a retracted configuration.
Figure 4:
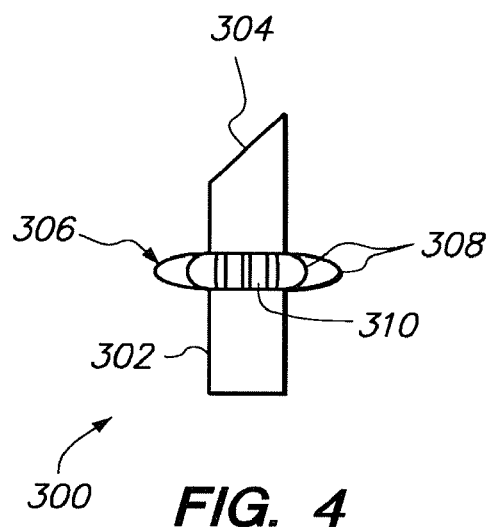
FIG. 4 is a plan view of the ablation probe of FIG. 3, wherein the ablative elements are particularly shown in a deployed configuration.

FIG. 3 illustrates a tissue ablation probe 300 constructed in accordance with another embodiment of the present invention. The ablation probe 300 includes a cannula having proximal portion 302 and distal portion 304, and a cage electrode array 306 that includes individual electrodes 308 disposed between proximal portion 302 and distal portion 304. The ends of each individual electrode of cage electrode array 306 may be coupled or attached to proximal portion 302 and distal portion 304. In some embodiments, proximal portion 302 and distal portion 304 are coupled together by the cage electrode array 306. In other embodiments, proximal portion 302 and distal portion 304 may be coupled using another structure, e.g., a mandrel 310 illustrated in FIG. 4. When pressure or force is exerted (e.g., on a handle, proximal end of proximal portion 302, mandrel, etc.), each of the individual electrodes of cage electrode array 306 bows outward, creating a shaped deployment (e.g. an ellipsoid), as illustrated in FIG. 4. By forcing the electrodes outwards, the cage electrode array 306 may be deployed into surrounding tissue and RF energy supplied to ablate the desired tissue. The cage electrode array 306 may be configured to form a pre-determined shape to generate a desired ablation burn pattern. In an optional embodiment, a handle (not shown) that holds the mandrel 310 can be configured to lock the positions of the proximal and distal cannula portions 302, 304 in both the retracted and deployed positions. This can be achieved with threads or luer locks.

The individual electrodes 308 of the array 306 may be alternately configured as live (i.e., supplying an electrical current, DC or AC) and ground leads. As another embodiment, one side of the electrodes in cage electrode array 306 may be live and the other half may be ground leads. In other embodiments, the mandrel 310 may have an area that, when cage electrode array 306 is deployed, becomes exposed. The exposed area acts as a ground for the live electrodes of cage electrode array 306. In other embodiments, only select electrodes 308 of the array 306 may be operated to further shape the profile of the RF energy to the desired shape. Thus, it can be appreciated that, like the ablation probe 100, the ablation probe 300 may have a monopolar or bipolar electrode configuration.

Figure 5:
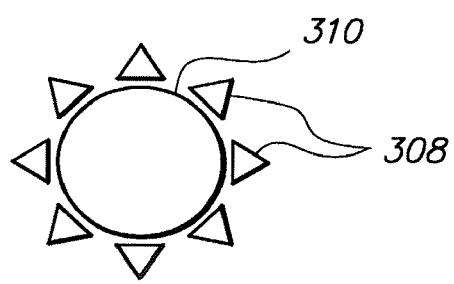
FIG. 5 is a cross-sectional view of the ablation probe of FIG. 3.

By moving proximal portion 302 and distal portion 304 towards each other, the individual electrodes 308 of cage electrode array 306 transversely bow outward from the cannula and into the surrounding tissue, as illustrated in FIG. 4. By forcing the electrodes outwards, cage electrode array 306 may be deployed into surrounding tissue and RF energy supplied to ablate the desired tissue. In some embodiments, the shape of each electrode of cage electrode array 306 may be configured to aid the deployment into different types of tissue (e.g., soft tissue, bone, and others). In one embodiment, the electrodes of the array 306 may be shaped to enable each electrode to cut into tissue when the electrode array is deployed, thereby aiding penetration of the array and improving ablation effectiveness. For example, FIG. 5 illustrates the electrodes 308 with triangular cross-sections, with one of the corners of the triangles (i.e., the outer edge of the electrodes 308) forming the cutting implement as the electrodes bow outward.

Having described the structure of the tissue ablation probes, their use in treating bone tissue, and specifically, a tumor (e.g., osteoid osteoma) within the cortical portion of a bone.

Figure 6A:
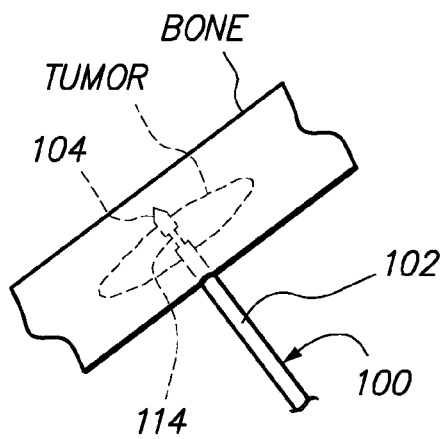
FIGS. 6A-6C are perspective views illustrating one method of operating the ablation probe of FIG. 1 to treat a bone tumor.
Figure 6B:
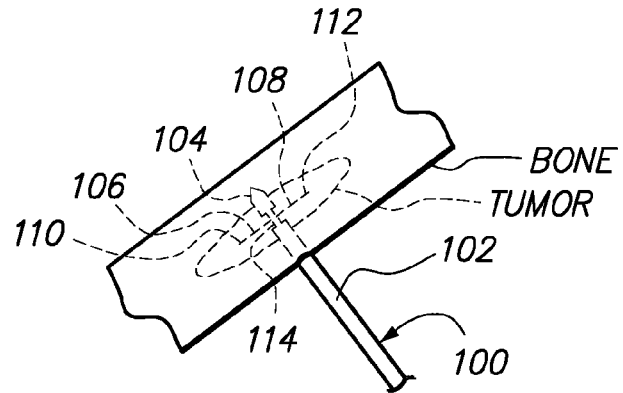
Figure 6C:
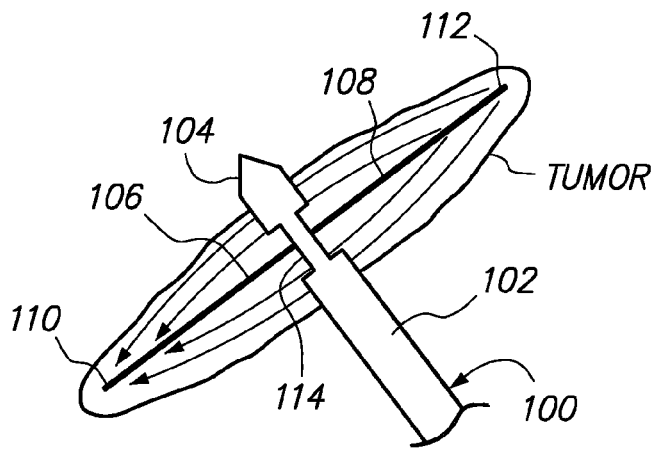

Referring now to FIGS. 6A-6C, the operation of the ablation probe 100 in treating an elliptically shaped tumor will now be described. First, the ablation probe 100 is percutaneously introduced into the cortical region of the bone in a conventional manner, such that the distal portion 104 of the cannula 102 is centered within the tumor, (i.e., half of the tumor is disposed on one side of the cannula 102 and the other half of the tumor is disposed on the other side of the cannula 102) (FIG. 6A). In addition, the electrode openings 114 should be centered within the tumor (i.e., half of the tumor disposed above the electrode openings 114 and the other half of the tumor disposed below the electrode openings 114). Next, the electrodes 106 and 108 are transversely deployed out from the cannula 102 in opposite directions via the openings 114, such that the tips 110 and 112 of the respective electrodes 106 and 108 advance through the tumor (FIG. 6B). As illustrated, the electrodes 106 and 108 are advanced until the respective tips 110 and 112 are located at the periphery of the tumor. Next, RF energy is conveyed between the electrodes 106 and 108 into the tumor in a bipolar configuration, thereby ablating the tumor (FIG. 6C). Alternatively, the RF energy may be conveyed from the electrodes 106 and 108 in a monopolar configuration. As can be seen, the conveyed RF energy (shown by the arrows) has an elliptical profile that matches the elliptical shape of the tumor, thereby allowing the tumor to be efficiently treated with minimal damage to the surrounding healthy bone tissue. The electrodes 106 and 108 can then be retracted within the cannula 102, and the ablation probe 200 removed from the patient in a conventional manner.

Figure 7A:
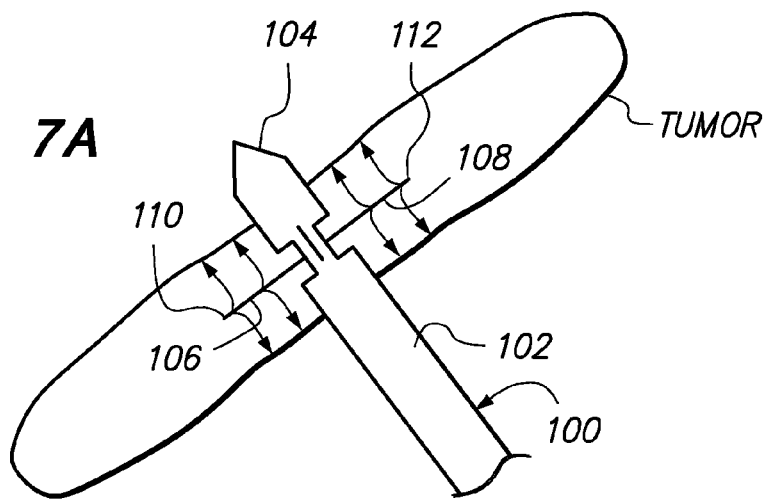
FIGS. 7A-7C are perspective views illustrating another method of operating the ablation probe of FIG. 1 to treat a bone tumor.
Figure 7B:
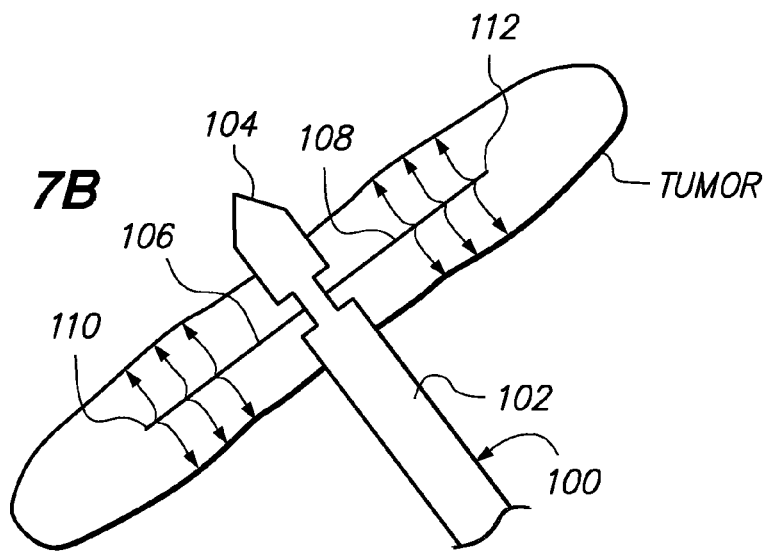
Figure 7C:
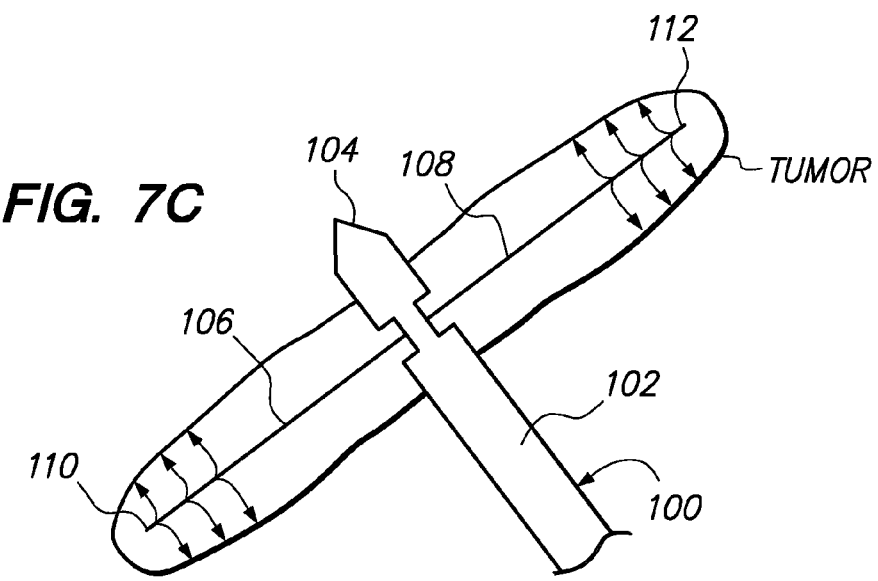

In an optional method, the electrodes 106 and 108 may be incrementally deployed, and RF energy can be conveyed from the electrodes 106 and 108 between the deployments. Such a technique lends itself well to bone tumors that are too elongated to be treated with only one ablation. For example, referring to FIGS. 7A-7C, the electrodes 106 and 108 can be deployed from the cannula 102 a first distance, and RF energy can be conveyed from the electrodes 106 and 108 to ablate the center of the tumor (FIG. 7A). The electrodes 106 and 108 can be advanced further from the cannula 102 a second greater distance, and RF energy can be conveyed from the electrodes 106 and 108 to extend the ablation outward from the center of the tumor (FIG. 7B). And then the electrodes 106 and 108 can be advanced even further from the electrodes 106 and 108 to complete the ablation of the bone tumor (FIG. 7C). As can be seen, the ablation energy can be delivered in a monopolar arrangement. Alternatively, the ablation energy is delivered in a bipolar arrangement.

Figure 8A:
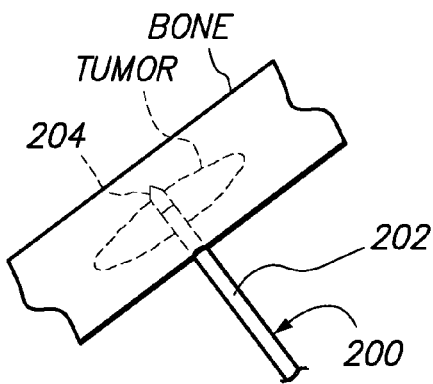
FIGS. 8A-8C are perspective views illustrating a method of operating the ablation probe of FIG. 2 to treat a bone tumor.
Figure 8B:
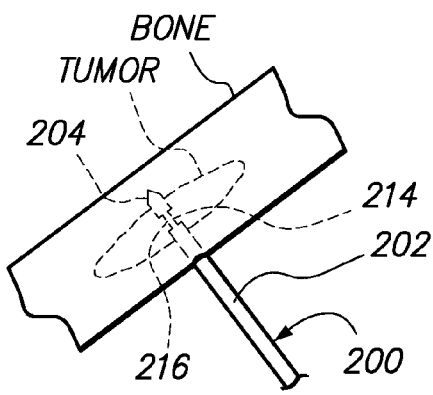
Figure 8C:
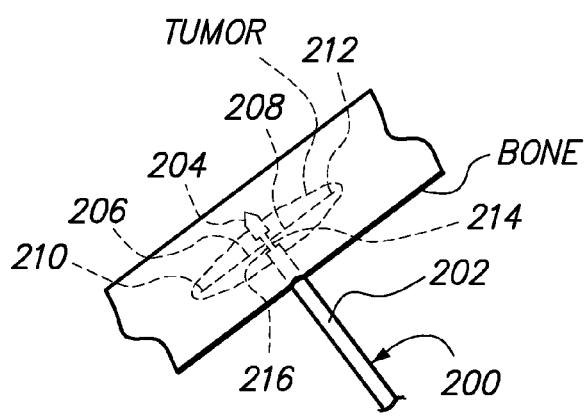

Referring now to FIGS. 8A-8C, the operation of the ablation probe 200 in treating an elliptically shaped tumor will now be described. First, the ablation probe 200, while the distal and proximal cannula portions 202 and 204 are compressed together to seal the opening 216, is percutaneously introduced into the cortical region of the bone in a conventional manner, such that the distal cannula portion 204 and the opening 216 are centered within the tumor (FIG. 8A). Next, distal cannula portion 204 is distally advanced relative to the proximal cannula portion 202, thereby exposing the opening 216 (FIG. 8B). The electrodes 206 and 208 are transversely deployed out from the opening 216, such that the tips 210 and 212 of the respective electrodes 206 and 208 advance through the tumor (FIG. 8C), and RF energy is conveyed from the electrodes 206 and 208 into the tumor, thereby ablating the tumor in the same manner illustrated in FIG. 6C. The electrodes 206 and 208 can then be retracted within the cannula, the distal cannula portion 204 can be proximally advanced relative to the proximal cannula portion 202 to seal the opening 216, and the ablation probe 200 removed from the patient.

Figure 9A:
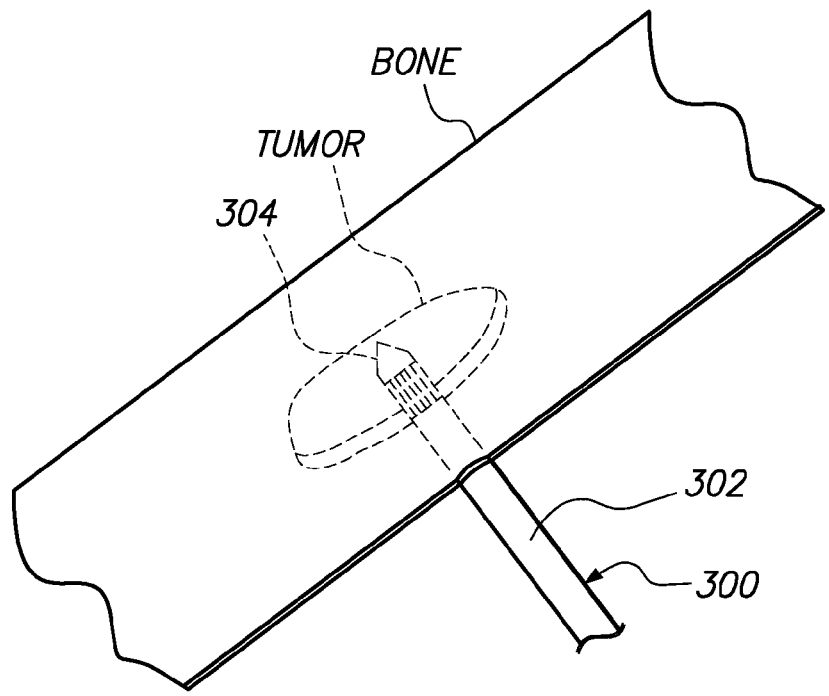
FIGS. 9A-9D are perspective views illustrating a method of operating the ablation probe of FIG. 3 to treat a bone tumor.
Figure 9B:
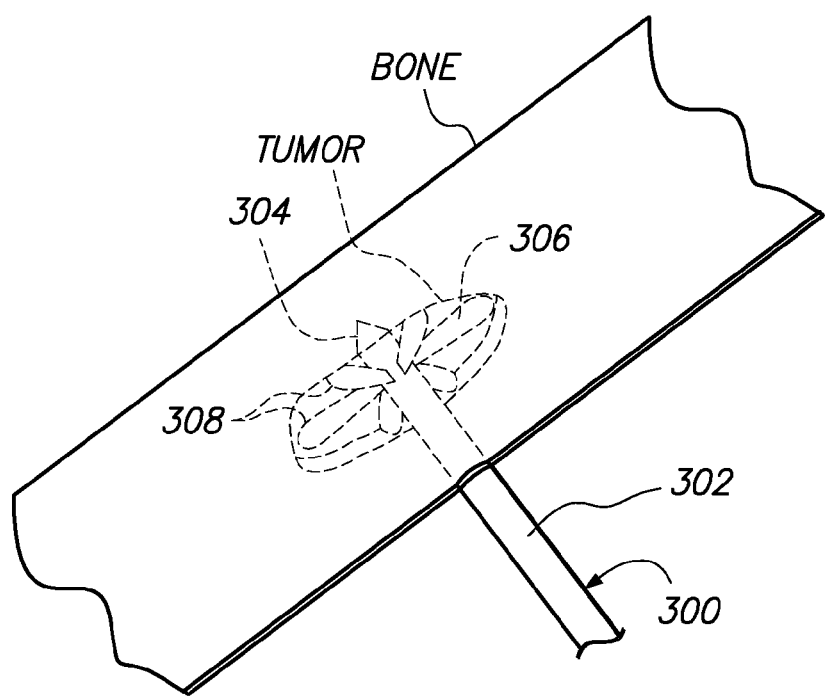
Figure 9C:
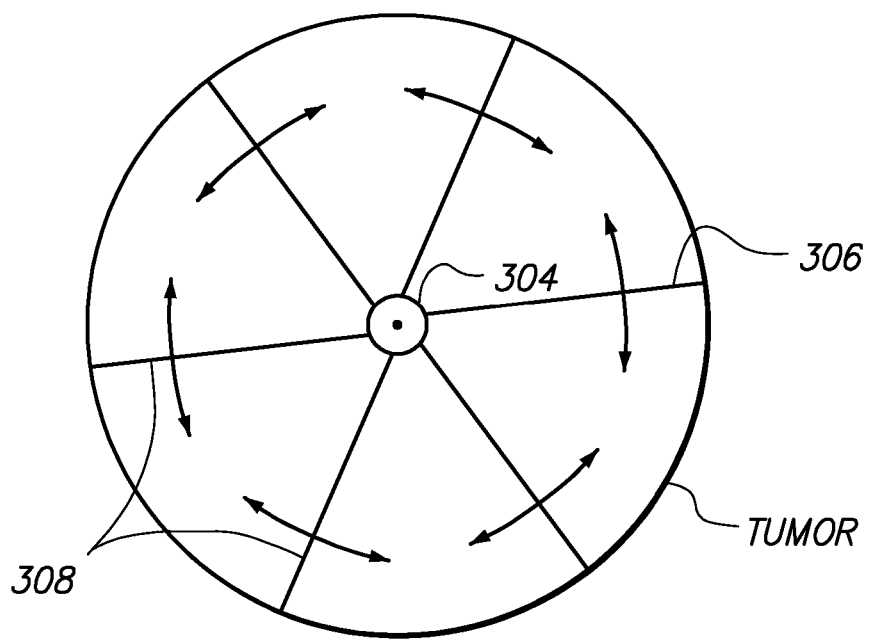
Figure 9D:
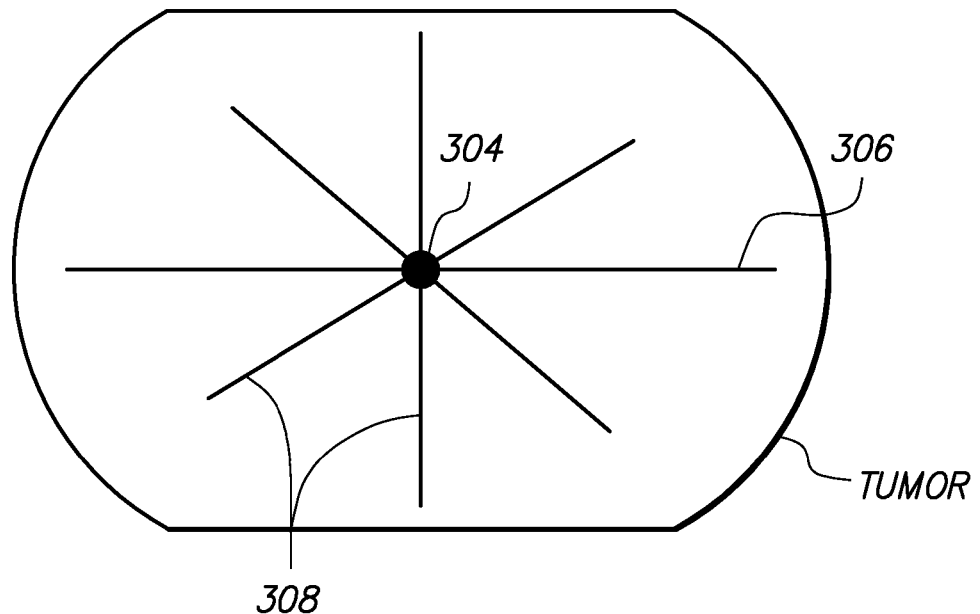

Referring now to FIGS. 9A-9C, the operation of the ablation probe 300 in treating a disk-shaped tumor will now be described. First, the ablation probe 300 is percutaneously introduced into the cortical region of the bone in a conventional manner, such that the distal cannula portion 304 is centered within the tumor (FIG. 9A). Next, the electrodes 308 of the array 306 are transversely deployed out from the cannula in a plane that coincides with the major plane of the flattened tumor by displacing the distal cannula portion 304 relative to the proximal cannula portion 302 to bow the electrodes 308 outward into the tissue (FIG. 9B). Next, RF energy is conveyed from the electrode array 306 into the tumor in a bipolar configuration, thereby ablating the tumor (FIG. 9C). Alternatively, the RF energy may be conveyed from the electrodes 308 in a monopolar configuration. As can be seen, the conveyed RF energy has a disk-like profile that matches the disk shaped tumor, thereby allowing the tumor to be efficiently treated with minimal damage to the surrounding healthy bone tissue. Alternatively, the lengths of the electrodes 308 may be adjusted to manipulate the RF energy profile to match the shape of the tumor (FIG. 9D). The distal cannula portion 304 can then be displaced distally relatively to the proximal cannula portion 302 to retract the electrodes 308, and the ablation probe 300 removed from the patient in a conventional manner.

Although the foregoing embodiments have been described in some detail for purposes of clarity of understanding, the implementation of these and other embodiments of the invention are not limited to the details and examples provided above.

What is claimed:

1. A method of treating bone tissue, comprising:
   introducing an ablation probe into bone tissue, wherein the ablation probe comprises a proximal portion and a distal portion;

distally advancing the ablation probe distal portion relative to the ablation probe proximal portion, thereby exposing an opening between the ablation probe distal portion and the ablation probe proximal portion;

deploying at least one ablative element transversely from the ablation probe opening into the bone tissue; and conveying ablation energy from the at least one ablative element to ablate the bone tissue.

2. The method of claim 1, wherein the at least one ablative element comprises a pair of ablative elements, and wherein the pair of ablative elements are transversely deployed from the ablation probe opening in opposite directions.

3. The method of claim 1, wherein the conveyed ablation energy has a non-spherical profile.

4. The method of claim 1, wherein the conveyed ablation energy has an elongated profile.

5. The method of claim 1, wherein the at least one ablative element comprises a distal tip, and the at least one ablative element is deployed into the bone tissue by advancing the distal tip through the bone tissue.

6. The method of claim 1, wherein the bone tissue is a tumor.

7. The method of claim 6, wherein the tumor is an osteoid osteoma.

8. The method of claim 1, wherein the probe is percutaneously introduced into the bone tissue.

9. A method of treating bone tissue, comprising:
introducing a probe into bone tissue, wherein the probe comprises a distal portion and a proximal portion;

distally advancing the probe distal portion relative to the probe proximal portion, thereby exposing an opening between the probe distal portion and the probe proximal portion;

deploying at least one electrode transversely from the probe opening into the bone tissue; and conveying radio frequency (RF) energy from the at least one electrode into the bone tissue.

10. The method of claim 9, wherein the at least one electrode comprises a pair of electrodes, and wherein the pair of electrodes are transversely deployed from the probe opening in opposite directions.

11. The method of claim 9, wherein the conveyed RF energy results in the ablation of the bone tissue.

12. The method of claim 9, wherein the conveyed RF energy has a non-spherical profile.

13. The method of claim 9, wherein the conveyed RF energy has an elongated profile.

14. The method of claim 9, wherein the at least one electrode comprises a distal tip, and the at least one electrode is deployed into the bone tissue by advancing the distal tip through the bone tissue.

15. The method of claim 9, wherein the bone tissue is a tumor.

16. The method of claim 15, wherein the tumor is an osteoid osteoma.

17. The method of claim 9, wherein the probe is percutaneously introduced into the bone tissue.

* * * * *